(12) United States Patent
Heider et al.

(10) Patent No.: US 6,943,263 B2
(45) Date of Patent: Sep. 13, 2005

(54) METHOD FOR PRODUCING BIS (TRIFLUOROMETHYL)IMIDO SALTS

(75) Inventors: Udo Heider, Winchester (GB); Michael Schmidt, Seeheim-Jugenheim (DE); Peter Sartori, Utting (DE); Nikolai Ignatyev, Duisburg (DE); Andrij Kucherina, Duisburg (DE); Ludmila Zinovyeva, Duisburg (DE)

(73) Assignee: Merck Patent GmbH, Darmstadt (DE)

( * ) Notice: Subject to any disclaimer, the term of this patent is extended or adjusted under 35 U.S.C. 154(b) by 65 days.

(21) Appl. No.: 10/468,022

(22) PCT Filed: Jan. 22, 2002

(86) PCT No.: PCT/EP02/00582

§ 371 (c)(1),
(2), (4) Date: Aug. 14, 2003

(87) PCT Pub. No.: WO02/064542

PCT Pub. Date: Aug. 22, 2002

(65) Prior Publication Data

US 2004/0073052 A1 Apr. 15, 2004

(30) Foreign Application Priority Data

Feb. 14, 2001 (DE) .......................... 101 07 118

(51) Int. Cl.$^7$ .............................. C07F 1/00; C07F 3/00; H01M 8/08
(52) U.S. Cl. .......................... 556/110; 556/118; 429/46
(58) Field of Search ............... 556/110, 118; 429/46

(56) References Cited

U.S. PATENT DOCUMENTS 3,897,495 A    7/1975    Bayer 6,582,849 B1   6/2003    Heider et al.

FOREIGN PATENT DOCUMENTS

| DE | 2101107 | 8/1972 |
|---|---|---|
| EP | 1081129 | 3/2001 |
| WO | WO 0046180 | 8/2000 |
| WO | WO 02064542 | 8/2002 |

OTHER PUBLICATIONS

H. G. Ang et al., "The Chemistry of Bis(trifluoromethyl)amino Compounds," Department of Chemistry, University of Singapore, Singapore.

Gmelin Handbook of Inorganic Chemistry Fluor, 1981, 8$^{th}$ Edition, pp. 125–153, part 9, Springer Veslag: Beslin, Heidelberg, New York.

A. Haas, Gemlin Handbook of Inorganic Chemistry Fluor, pp. 196–214.

Ghulam Sarwar, "Insertion of tetrafluoroethylene and trifluorochloroethylene into nitrogen–chlorine bonds; A new route to perfluoroazaalkenes," Inorganic Chemistry, 1989, pp. 2187–2189, vol. 28, American Chemical Society.

John A. Young et al., "Fluorocarbon nitrogen compounds. III. Some reactions of Bis–(trifluoromethyl)–amine," Jul. 20, 1958, pp. 3604–3606, vol. 80.

Gemlin Handbook of Inorganic Chemistry, 1981, 8$^{th}$ Edition, pp. 44–45, part 9.

A. I. Gonter et al., 1975, pp. 2279–2282.

Primary Examiner—Porfirio Nazario-Gonzalez
(74) Attorney, Agent, or Firm—Millen White Zelano & Branigan, P.C.

(57) ABSTRACT

The present invention relates to a novel process for the preparation of bis(trifluoromethyl)imido salts of the general formula (I):

$$[M^{a+}][N(CF_3)_2]_a \qquad (I).$$

21 Claims, 3 Drawing Sheets

METHOD FOR PRODUCING BIS(TRIFLUOROMETHYL)IMIDO SALTS

The present invention relates to novel processes for the preparation of bis(trifluoromethyl)imido salts of the general formula (I):

$$M^{a+}[(N(CF_3)_2)^-]_a \qquad (I)$$

The chemistry of the bis(trifluoromethyl)imido anion is generally based on the chemical reaction of perfluoro(2-azapropene), $CF_3N=CF_2$, as starting material (H. G. Ang and Y. C. Syn, Advances in Inorganic Chemistry and Radiochemistry, Vol. 16 (1974), pp. 1–64; A. Haas, Gmelin Handbook of Inorganic Chemistry, 8th Edition, Springer Verlag: Berlin, Heidelberg, New York (1991), Part 9, pp. 125–153; A. Haas, Gmelin Handbook of Inorganic Chemistry, 8th Edition, Springer Verlag: Berlin, Heidelberg, New York (1991), Suppl. Vol. 6, pp. 196–214). This compound can be prepared by fluorination of $CCl_3N=CCl_2$ using NaF in sulfolane at 105° C. in a yield of 78% (E. Klauke, H. Holtschmidt, K. Findeisen, Farbenfabriken Bayer AG, DE-A1-2101107 (1971/1972)) or by photolysis of $CF_3N-(CF_2CFCl_2)Cl$ (G. Sawar, R. L. Kirchmeier and J. M. Shreeve, Inorg. Chem. 28 (1989, pp. 2187–2189)) in gas at room temperature (boiling point −33° C.), with special industrial apparatuses being necessary for the said compound.

Di[bis(trifluoromethyl)imido]mercury, $Hg[N(CF_3)_2]_2$, which is very reactive, was synthesised for the first time by Young and his co-workers (J. A. Young, S. N. Tsoukalas and R. D. Dresdner, J. Am. Chem. Soc. 80 (1958), pp. 3604–3606). This compound is a good reagent for the introduction of $N(CF_3)_2$ groups into organic molecules (H. G. Ang and Y. C. Syn, see above; A. Haas, Gmelin Handbook of Inorganic Chemistry, 8th edition, Springer Verlag: Berlin, Heidelberg, New York (1981), Part 9, pp. 45–46), but is not a very stable compound since it is extremely sensitive to moisture. The synthesis of $Hg[N(CF_3)_2]_2$ is difficult, time-consuming and requires special industrial apparatuses and expensive starting materials.

Caesium bis(trifluoromethyl)imide, $[Cs]^+[N(CF_3)_2]^-$, is a further option for the synthesis of bis(trifluoromethyl)amino compounds. This salt is prepared by simply passing perfluoro(2-azapropene) into a solution of caesium fluoride in dry acetonitrile (A. F. Gontar, E. G. Bykovskaja and I. L. Knunyants, IZV. Akad. Nauk SSSR, Otd. Khim, Nauk (1975), pp. 2279–2282).

The disadvantage of this method consists in the formation of a dimeric product through the reaction of the starting material perfluoro(2-azapropene) with the caesium salt that has already formed. This reaction is unavoidable and results in the formation of complex product mixtures.

However, $N(CF_3)_2$ anions are readily accessible through the reaction of some metal fluorides with N,N-bis(trifluoromethyl)perfluoroalkanesulfonamides or -acylamides ["$N(CF_3)_2$ anion preparation, and its use", EP 99 101 982]. This process enables the generation of Na, K, Rb, Cs, Ag, Cu(II) and Hg(II) salts with $N(CF_3)_2$ anions. However, the analogous reaction of N,N-bis(trifluoromethyl)perfluoroalkanesulfonamides or -acylamides with other metal fluorides (for example $ZnF_2$ and $CdF_2$) progresses only very slowly due to the poor solubility of these fluorides in organic solvents.

Figure 1:
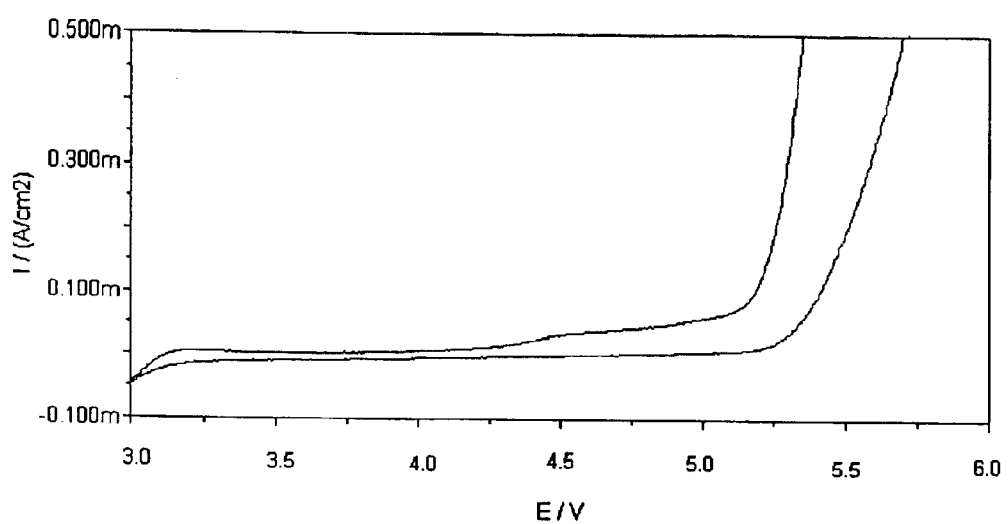
FIG. 1 is a graphical depiction of the electrochemical stability of an exemplary embodiment of the invention.

The object of the present invention was therefore to provide an improved process for the preparation of bis(trifluoromethyl)imido salts.

The object according to the invention is achieved by a process for the preparation of bis(trifluoromethyl)imido salts of the general formula (I)

$$[M^{a+}][(N(CF_3)_2)^-]_a \qquad (I)$$

in which $M^{a+}$ is a monovalent or divalent cation, and a=1 or 2, characterised in that at least one trifluoromethanesulfonate of the general formula (II)

$$[M^{a+}][(OSO_2CF_3)^-]_a \qquad (II)$$

in which $M^{a+}$ is a monovalent or divalent cation, and a=1 or 2, is reacted with bis(trifluoromethyl)imidorubidium in solution, and the resultant bis(trifluoromethyl)imido salt of the general formula (I) is, if desired, purified and/or isolated by conventional methods.

Preference is given to processes according to the invention in which $M^{a+}$ is a sodium, potassium, caesium, copper or silver cation, and a=1.

Particular preference is given to processes according to the invention in which $M^{a+}$ is a mercury, copper, zinc or cadmium cation, and a=2.

Particular preference is also given to processes according to the invention in which a=1 and $M^{a+}$ is a cation of the general formula (III)

$$[(R_b^1 R_c^2 R_d^3 R_e^4]A_x)_y Kt]^+ \qquad (III)$$

in which

Kt=N, P, As, Sb, S or Se,

A=N, P, P(O), O, S, S(O), $SO_2$, As, As(O), Sb or Sb(O), $R^1$, $R^2$, $R^3$ and $R^4$ are identical or different and are H, halogen, substituted and/or unsubstituted alkyl $C_nH_{2n+1}$, substituted and/or unsubstituted $C_{1-18}$-alkenyl having one or more double bonds, substituted and/or unsubstituted $C_{1-18}$-alkynyl having one or more triple bonds, substituted and/or unsubstituted cycloalkyl $C_mH_{2m-1}$, monosubstituted, polysubstituted and/or unsubstituted phenyl, substituted and/or unsubstituted heteroaryl;

where n=1–18, m=3–7, x=0 or 1, y=1–4, y=1 for x=0, where b, c, d and e are each=0 or 1, where b+c+d+e≠0, A may be included in various positions in $R^1$, $R^2$, $R^3$ and/or $R^4$, Kt may be included in a cyclic or heterocyclic ring, the groups bonded to Kt may be identical or different.

The processes according to the invention also enable the preparation of novel bis(trifluoromethyl)imido salts which are difficult to access, such as, for example, cadmium, zinc or copper(I) $N(CF_3)_2$ salts. Novel salts therefore represent a further subject-matter of the present invention.

The salts prepared in accordance with the invention can be used alone or in mixtures with other salts as conductive salts or additives in electrolytes. Besides the salt or salt mixtures, the electrolytes also comprise solvents or solvent mixtures.

These electrolytes are employed in electrochemical cells (such as, for example, primary and secondary batteries). They are preferably employed in capacitors and supercapacitors.

The starting materials bis(trifluoromethyl)imidorubidium and the trifluoromethanesulfonate salts are both readily soluble in a number of organic solvents. In addition, metal triflates are commercially available from a number of companies.

The reaction of $Rb[N(CF_3)_2]$ and metal triflates at room temperature or below takes place rapidly, for example in accordance with the following general reaction scheme:

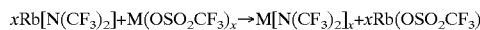

$$xRb[N(CF_3)_2]+M(OSO_2CF_3)_x \rightarrow M[N(CF_3)_2]_x+xRb(OSO_2CF_3)$$

In the process according to the invention, the conversion to a bis(trifluoromethyl)imido salt of the general formula (I) is preferably carried out at a temperature of from −60 to +60° C., particularly preferably from −50 to +50° C., very particularly preferably at from −45 to +30° C.

Preferred solvents for the conversion to a bis(trifluoromethyl)imido salt of the general formula (I) are organic solvents, particularly preferably polar organic solvents.

Very particularly preferred solvents for the conversion to a bis(trifluoromethyl)imido salt of the general formula (I) are the solvents acetonitrile, benzonitrile, dimethoxyethane and/or propionitrile or a mixture of acetonitrile, benzonitrile, dimethoxyethane and/or propionitrile.

Preferred solvents according to the invention comprise ≦0.1% by weight of water, preferably ≦0.01% by weight of water, particularly preferably ≦0.005% by weight of water.

In the preferred processes according to the invention, the trifluoromethanesulfonate salt of the general formula (II) or the bis(trifluoromethyl)imidorubidium is employed in a molar excess of ≦3% or particularly preferably in equimolar amounts.

The rubidium triflate formed by the process according to the invention has limited solubility in organic solvents and can be separated off from the reaction mixture as a solid at low temperatures.

Preferred processes according to the invention are therefore those in which the bis(trifluoromethyl)imido salt of the general formula (I) is purified by filtration at a temperature of from −90 to +30° C., particularly preferably at from −70 to +20° C., after removal of the solvent.

Further purification of a bis(trifluoromethyl)imido salt of the general formula (I) is possible by extraction with dichloromethane and/or hexane and/or diethyl ether. Extraction with dichloromethane is a preferred variant of the present invention.

The invention is explained below with reference to examples. These examples serve merely to explain the invention and do not restrict the general inventive idea.

EXAMPLES

Example 1

Synthesis of Bis(trifluoromethyl)imidosilver Salt

A solution of $Rb[N(CF_3)_2]$ salt prepared from 0.083 g (0.79 mmol) of rubidium fluoride and 0.227 g (0.79 mmol) of $CF_3SO_2N(CF_3)_2$ in 3.2 ml of dry acetonitrile was added to a solution, cooled to −20° C., of 0.205 g (0.79 mmol) of $AgOSO_2CF_3$ in 1.8 ml of dry acetonitrile with stirring. The mixture was stirred at −20° C. for one hour. A white sediment formed in the process. The solvent acetonitrile was removed by suction filtration at −20° C., and 4 ml of dry dichloromethane were added to the residue. After the mixture had been stirred at −20° C. for ten minutes, the solution was separated from the residue, and the solvent was removed by suction filtration at −20° C. 0.149 g of $Ag[N(CF_3)_2] \cdot CH_3CN$ was obtained as a white crystalline substance, as demonstrated by analysis. The yield was 62.3%.

Analysis (amperometric titration):

Yield: 35.76% ($Ag^+$);

Theoretical value for $Ag[N(CF_3)_2] \cdot CH_3CN$: 35.85% ($Ag^+$);

$^{19}F$ NMR spectrum (solvent $CD_2Cl_2$, reference substance $CCl_3F$), ppm: −44.56 s ($CF_3$)

$^1H$ NMR spectrum (solvent $CD_2Cl_2$, reference substance TMS), ppm: 2.08 s ($CH_3CN$)

$^{109}Ag$ NMR spectrum (solvent $CD_2Cl_2$, reference point: chemical shift of 1M $AgNO_3$ in $D_2O$ set to 0), ppm: 316.23 s, Ag

Example 2

Synthesis of Bis(trifluoromethyl)imidocopper(I) Salt

A solution of $Rb[N(CF_3)_2]$ salt prepared from 0.080 g (0.766 mmol) of rubidium fluoride and 0.218 g (0.766 mmol) of $CF_3SO_2N(CF_3)_2$ in 3.2 ml of dry acetonitrile was added at room temperature to a solution of 0.194 g (0.766 mmol) of $CuOSO_2CF_3 \cdot CH_3CN$ in 1.8 ml of dry acetonitrile with stirring. The mixture was stirred for one hour. A white sediment formed in the process. The solvent acetonitrile was removed by suction filtration at room temperature, and 4 ml of dry dichloromethane were added to the residue. After the mixture had been stirred at room temperature for ten minutes, the solution was separated from the residue, and the solvent was removed by suction filtration at room temperature. 0.150 g of $Cu[N(CF_3)_2] \cdot CH_3CN$ was obtained as a white crystalline substance, as demonstrated by analysis. The yield was 76.5%.

$^{19}F$ NMR spectrum (solvent $CD_2Cl_2$, reference substance $CCl_3F$), ppm: −44.79 s ($CF_3$)

$^1H$-NMR spectrum (solvent $CD_2Cl_2$, reference substance TMS), ppm: 2.03 s, $CH_3CN$

Example 3

Synthesis of Bis(trifluoromethyl)imidozinc Salt

A solution of $Rb[N(CF_3)_2]$ salt prepared from 0.080 g (0.766 mmol) of rubidium fluoride and 0.218 g (0.766 mmol) of $CF_3SO_2N(CF_3)_2$ in 3.2 ml of dry propionitrile was added at −45° C. to a solution of 0.155 g (0.383 mmol) of $Zn(OSO_2CF_3)_2 \cdot CH_3CN$ in 1.8 ml of dry propionitrile with stirring. The mixture was stirred for one hour at −45° C. A white sediment formed in the process. The mixture was then cooled to −78° C. and left at this temperature without stirring for two hours. The solvent was removed by suction filtration, a small amount of $CD_3CN$ (about 30%) was added, and the mixture was characterised by $^{19}F$ NMR spectroscopy at −45° C.

The signal at −44.83 ppm is assigned to $Zn[N(CF_3)_2]_2$, which is coordinated with the solvent.

In order to isolate the salt, the solvent was removed by suction filtration at −30° C., and the white solid which remained was, after dissolution in dry $CD_2Cl_2$, employed for NMR spectroscopy. The NMR spectrum showed the presence of the propionitrile in the crystal structure of the $Zn[N(CF_3)_2]_2 \cdot C_2H_5CN$ salt. This salt has only low stability as analysis substance at room temperature.

$^{19}F$ NMR spectrum at −40° C. (solvent $CD_2Cl_2$, reference substance $CCl_3F$), ppm: −45.97 s ($CF_3$, the position of the signal is concentration-dependent)

$^1H$ NMR spectrum at −40° C. (solvent $CD_2Cl_2$, reference substance TMS), ppm: 1.08 t ($CH_3$); 2.25 q ($CH_2$), $C_2H_5CN$ Example 4

Synthesis of Bis(trifluoromethyl)imidocadmium Salt

A solution of $Rb[N(CF_3)_2]$ salt prepared from 0.080 g (0.766 mmol) of rubidium fluoride and 0.218 g (0.766 mmol) of $CF_3SO_2N(CF_3)_2$ in 3.2 ml of dry propionitrile was added at −45° C. to a solution of 0.188 g (0.383 mmol) of $Cd(OSO_2CF_3)_2 \cdot 2CH_3CN$ in 1.8 ml of dry propionitrile with stirring. The mixture was stirred for one hour at −45° C. A white sediment formed in the process, the mixture was then cooled to −78° C. and left at this temperature without stirring for two hours. The solvent was removed by suction filtration, a small amount of $CD_3CN$ (about 30% by volume) was added, and the mixture was characterised by $^{19}F$ NMR spectroscopy at −40° C. The signal at −42.53 ppm is assigned to $Cd[N(CF_3)_2]_2$, which is coordinated with the solvent. At room temperature, the signal of the $N(CF_3)_2$ group in the $^{19}F$ NMR spectrum shifts to −45.39 ppm. The $Cd[N(CF_3)_2]_2 \cdot nC_2H_5CN$ salt has only low stability as analysis substance at room temperature.

Example 5

Electrochemical Stability of $[N(C_2H_5)_4][N(CF_3)_2]$

In each case, a number of cyclic voltammograms were recorded successively in a measurement cell with platinum electrode, lithium counterelectrode and lithium reference electrode. To this end, the potential was firstly increased, starting from the rest potential, to 6 V against $Li/Li^+$ at a rate of 20 mV/s and then returned to the rest potential. The electrolyte used was a solution of $[N(C_2H_5)_4][N(CF_3)_2]$ in propylene carbonate.

The characteristic curve shape shown in FIG. 1 is evident, with an oxidation potential $E_{ox}$ of greater than 5 V against $Li/Li^+$.

Example 6

Ionic Conductivity of an Electrolyte Based on $[N(C_2H_5)_4][N(CF_3)_2]$

Figure 2:
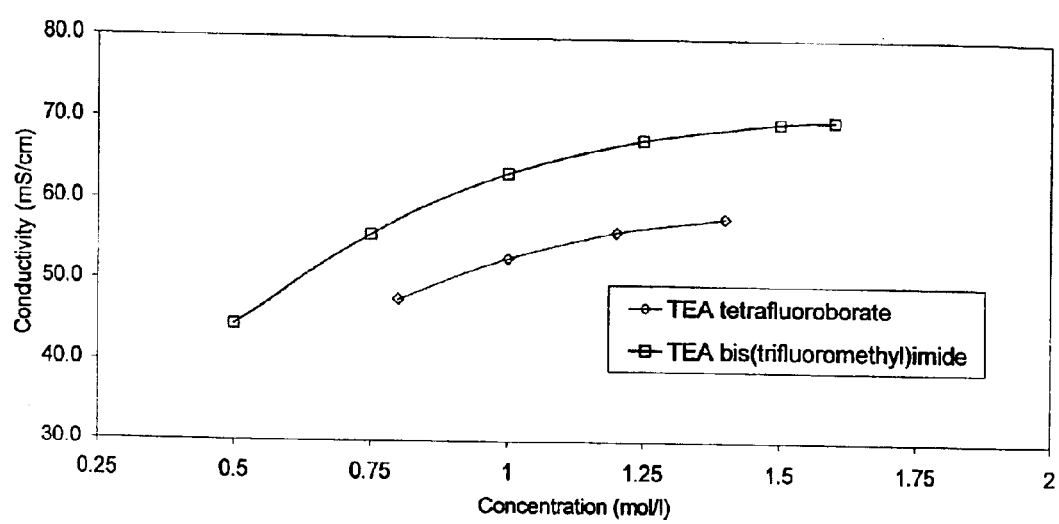
FIG. 2 is a graphical depiction of the conductivity of an exemplary embodiment of the present invention.
Figure 3:
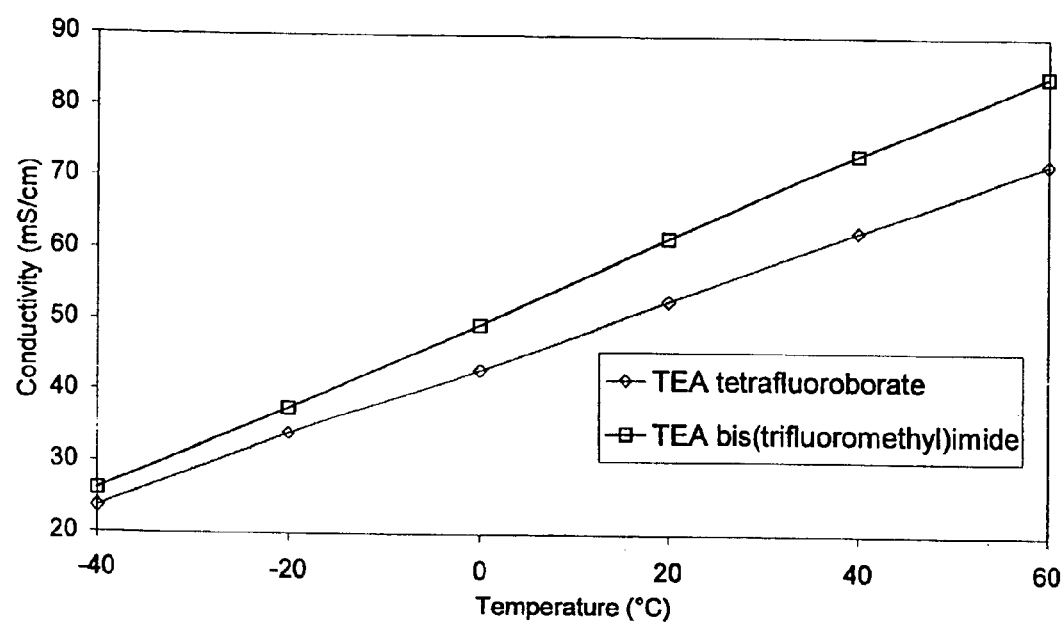
FIG. 3 is a graphical depiction of the conductivity of a comparative example.

With the aid of a 4-pole Knick conductometer, the conductivities of $[N(C_2H_5)_4][N(CF_3)_2]$ in acetonitrile were measured as a function of temperature and concentration of the conductive salt. In parallel, $[N(C_2H_5)_4][BF_4]$ was measured in acetonitrile. This system represents the current state of the art with respect to "supercapacitor" electrolytes and thus serves as reference. FIGS. 2 and 3 show the results obtained. They confirm that the novel system based on $[N(C_2H_5)_4][N(CF_3)_2]$ has significantly improved conductivities.

What is claimed is:

1. A process for the preparation of a bis(trifluoromethyl)imido salt of the general formula (I)

$$M^{a+}[(N(CF_3)_2)^-]_a \qquad (I)$$

wherein $M^{a+}$ is a monovalent or divalent cation, and a=1 or 2, comprising reacting at least one trifluoromethanesulfonate of the general formula (II)

$$[M^{a+}][(OSO_2CF_3)^-]_a \qquad (II)$$

wherein $M^{a+}$ is a monovalent or divalent cation, and a=1 or 2, with bis(trifluoromethyl)imidorubidium in solution, and the resultant bis(trifluoromethyl)imido salt of the general formula (I) is, if desired, purified and/or isolated.

2. A process according to claim 1, wherein $M^{a+}$ is a sodium, potassium, cesium, copper or silver cation, and a=1.

3. A process according to claim 1, wherein $M^{a+}$ is a mercury, copper, zinc or cadmium cation, and a=2.

4. A process according to claim 1, wherein a=1 and $M^{a+}$ is a cation of the general formula (III)

$$[(R_b^1 R_c^2 R_d^3 R_e^4]A_x)_y Kt]^+ \qquad (III)$$

wherein

Kt=N, P, As, Sb, S or Se,

A=N, P, P(O), O, S, S(O), $SO_2$As, As(O), Sb or Sb(O), $R^1$, $R^2$, $R^3$ and $R^4$ are identical or different and are H, halogen, substituted and/or unsubstituted alkyl $C_nH_{2n+1}$, substituted and/or unsubstituted $C_{1-18}$-alkenyl having one or more double bonds, substituted and/or unsubstituted $C_{1-18}$-alkynyl having one or more triple bonds, substituted and/or unsubstituted cycloalkyl $C_mH_{2m-1}$, monosubstituted, polysubstituted and/or unsubstituted phenyl, substituted and/or unsubstituted heteroaryl;

where n=1–18, m=3–7, x=0 or 1, y=1–4, y=1 for x=0, where b, c, d and e are each=0 or 1, where b+c+d+e≠0, A may be included in various positions in $R^1$, $R^2$, $R^3$ and/or R4, Kt may be included in a cyclic or heterocyclic ring, and the groups bonded to Kt may be identical or different.

5. A process according to claim 1, wherein the conversion to a bis(trifluoromethyl)imido salt of the general formula (I) is carried out at a temperature of −60–+60° C.

6. A process according to claim 1, wherein the conversion to a bis(trifluoromethyl)imido salt of the general formula (I) is carried out in an organic solvent.

7. A process according to claim 6, wherein the solvent used is acetonitrile, benzonitrile, dimethoxyethane and/or propionitrile or a mixture of acetonitrile, benzonitrile, dimethoxyethane and/or propionitrile.

8. A process according to claim 1, wherein the solvent comprises ≦0.1% by weight of water.

9. A process according to claim 1, wherein the trifluoromethanesulfonate salt of the general formula (II) or the bis(trifluoromethyl)imidorubidium is employed in a molar excess of ≦3% or in equimolar amounts.

10. A process according to claim 1, wherein the bis(trifluoromethyl)imido salt of the general formula (I) is purified by filtration after removal of the solvent.

11. A process according to claim 1, wherein the bis (trifluoromethyl)imido salt of the general formula (I) is purified by extraction with dichloromethane and/or hexane and/or diethyl ether.

12. A compound of the general formula (I)

$$M^{a+}[(N(CF_3)_2)^-]_a \qquad (I)$$

wherein $M^{a+}=Cd^{2+}$, $Zn^{2+}$ or $Cu^+$.

13. An electrolyte comprising at least one salt of the general formula (I) prepared according to claim 1.

14. An electrochemical cell comprising an electrolyte according to claim 13.

15. A process according to claim 1, wherein the conversion is carried out at a temperature of −50−+50° C.

16. A process according to claim 1, wherein the conversion is carried out at a temperature of −45−+30° C.

17. A process according to claim 1, wherein the conversion is carried out in a polar solvent.

18. A process according to claim 1, wherein the solvent comprises ≦0.01% by weight of water.

19. A process according to claim 1, wherein the solvent comprises ≦0.005% by weight of water.

20. A process according to claim 1, wherein the bis (trifluoromethyl)imido salt of the general formula (I) is purified by filtration at a temperature of −90−+30° C.

21. A process according to claim 1, wherein the bis (trifluoromethyl)imido salt of the general formula (I) is purified by filtration at a temperature of −70−+20° C.

* * * * *

UNITED STATES PATENT AND TRADEMARK OFFICE
CERTIFICATE OF CORRECTION

PATENT NO.        : 6,943,263 B2
APPLICATION NO. : 10/468022
DATED             : September 13, 2005
INVENTOR(S)       : Udo Heider et al.

It is certified that error appears in the above-identified patent and that said Letters Patent is hereby corrected as shown below:

Column 6, line 12, reads "or2," should read -- or 2, --
Column 6, line 27, reads "$SO_2As$," should read -- $SO_2$, As, --
Column 6, line 46, reads "R4" should read -- $R^4$ --

Signed and Sealed this

First Day of August, 2006

JON W. DUDAS
*Director of the United States Patent and Trademark Office*